United States Patent [19]

Inoue et al.

[11] Patent Number: 4,691,066

[45] Date of Patent: Sep. 1, 1987

[54] PROCESS OF PREPARING METACHLOROBENZOTRIFLUORIDE

[75] Inventors: Fumio Inoue, Sakado; Yutaka Katsuhara, Kawagoe; Koshi Okazaki, Saitama, all of Japan

[73] Assignee: Central Glass Company, Limited, Ube, Japan

[21] Appl. No.: 709,370

[22] Filed: Mar. 11, 1985

Related U.S. Application Data

[63] Continuation of Ser. No. 503,169, Jun. 10, 1983, abandoned.

[30] Foreign Application Priority Data

Jun. 18, 1982 [JP] Japan ................. 57-104004

[51] Int. Cl.$^4$ ............................................. C07C 17/12
[52] U.S. Cl. .................................... 570/144; 570/147
[58] Field of Search .................... 570/147, 145, 144

[56] References Cited

U.S. PATENT DOCUMENTS

2,707,197  4/1955  Souillard ............................. 570/208
3,234,292  2/1966  Robota et al. ....................... 570/144
4,155,940  5/1979  Marhold et al. ..................... 570/145

FOREIGN PATENT DOCUMENTS

963468  7/1950  France .

OTHER PUBLICATIONS

Groggins, *Unit Processes in Organic Synthesis, Halogenation*, pp. 237, 238, 265, 266.

*Primary Examiner*—J. E. Evans
*Assistant Examiner*—Joseph A. Boska
*Attorney, Agent, or Firm*—Schwartz, Jeffery, Schwaab, Mack, Blumenthal & Evans

[57] ABSTRACT

In the preparation of m-chlorobenzotrifluoride (m-CBTF) by reaction between benzotrifluoride and chlorine gas, a combination of a chloride of a metal having a valence of 3 to 6 and a small amount of iodine is used as catalyst. Alternative to iodine use can be made of an iodide that liberates iodine in the presence of chlorine. The catalyst exhibits high selectivity for m-CBTF and is effective for increasing the ratio of m-CBTF to p-CBTF in the reaction product.

3 Claims, No Drawings

PROCESS OF PREPARING METACHLOROBENZOTRIFLUORIDE

This application is a continuation of application Ser. No. 503,169 filed June 10, 1983, abandoned.

BACKGROUND OF THE INVENTION

This invention relates to a process of preparing m-chlorobenzotrifluoride by reaction between benzotrifluoride and chlorine in the presence of a catalyst.

In the chemical industry m-chlorobenzotrifluoride is a compound useful as an intermediate in the preparation of various organic substances including dyes, pigments, medicines and agricultural chemicals.

As is known, m-chlorobenzotrifluoride can be prepared by making chlorine react with benzotrifluoride in the presence of a catalyst to accomplish chlorine substitutation in the benzene nucleus. However, by this reaction it is impossible to convert benzotrifluoride exclusively to m-chlorobenzotrifluoride. The reaction product always contains considerable amounts of isomers, i.e. o- and p-chlorobenzotrifluorides, and dichlorobenzotrifluoride isomers. The isolation of m-chlorobenzotrifluoride formed by the reaction is difficult especially because of the small difference between the boiling point of m-chlorobenzotrifluoride (138.1° C.) and the boiling point of p-chlorobenzotrifluoride (139.2° C.). Therefore, there is a strong demand for a new technique to carry out monochlorination of benzotrifluoride with chlorine gas with high selectivity for m-chlorobenzotrifluoride and also with high ratio of m-chlorobenzotrifluoride to p-chlorobenzotrifluoride in the reaction product.

With respect to the above described reaction, U.S. Pat. No. 3,234,292 proposes to use a combination of ferric chloride and either sulfur chloride or sulfur dichloride as the catalyst. By this method, however, the selectivity for m-chlorobenzotrifluoride is too low and the ratio of the m-substitute to the p-isomer is also low. Besides, this method requires a long time to complete the reaction because of relatively low activity of the catalyst and suffers from low conversion efficiency of chlorine and, hence, can hardly be taken as suited to industrial practice.

SUMMARY OF THE INVENTION

It is an object of the present invention to provide an improved and industrially favorable process for the preparation of m-chlorobenzotrifluoride by reaction between benzotrifluoride and chlorine in the presence of a catalyst with enhanced selectivity for m-chlorobenzotrifluoride and with an increased ratio of m-chlorobenzotrifluoride to p-chlorobenzotrifluoride in the reaction product.

In a process according to the present invention chlorine gas is made to react with benzotrifluoride in the presence of a catalyst so as to form monochlorobenzotrifluoride, and the improvement according to the invention resides in that the catalyst is a combination of at least one chloride of a metal having a valence of 3 to 6 and either iodine or an iodide that liberates iodine in the presence of chlorine.

We have discovered that the coexistence of iodine with the metal chloride employed as the primary component of the catalyst is surprisingly effective for enhancement of selectivity for m-chlorobenzotrifluoride and also for effecting an increase in the ratio of m-chlorobenzotrifluoride to the p-isomer in the product of the chlorination reaction.

Due to the distinctive ability of the catalyst comprising iodine, the process according to the invention produces m-chlorobenzotrifluoride with high yield and facilitates the isolation of m-chlorobenzotrifluoride with high purity. Furthermore, the catalyst used in this process exhibits high activity so that chlorine gas reacts with benzotrifluoride with an enhanced efficiency. Therefore, the reaction can be completed in a relatively short time with the effect of increasing the production of m-chlorobenzotrifluoride per unit time, and, besides, operations for treatment of by-produced hydrogen chloride can be simplified.

The reaction in this process can be carried out at normal pressure and at temperatures not greatly different from room temperature.

DESCRIPTION OF THE PREFERRED EMBODIMENTS

In the process according to the invention, the primary component of the catalyst is a chloride of a metal having a valence of 3 to 6. In general it is suitable to use an anhydrous chloride.

As chlorides of metals having a valence of 3, iron(III) chloride, aluminum chloride, gallium trichloride, indium trichloride, thallium trichloride and molybdenum trichloride can be named as suitable examples. As chlorides of metals having a valence of 4, titanium tetrachloride, zirconium tetrachloride and hafnium chloride can be named as suitable examples. As chlorides of metals having a valence of 5, antimony pentachloride, molybdenum pentachloride, niobium pentachloride and tantalum pentachloride can be named as suitable examples. As chlorides of metals having a valence of 6, tungsten hexachloride can be named as a suitable example. If desired it is possible to use two or more of these metal chlorides in various combinations.

The secondary but essential component of the catalyst is iodine. Alternatively to iodine in molecular form, it is possible to use an iodide which readily decomposes in the presence of chlorine to liberate iodine. Examples of suitable iodides are alkali metal iodides such as LiI, NaI, KI, RbI and CsI and alkaline earth metal iodides such as $BeI_2$, $MgI_2$, $CaI_2$, $SrI_2$ and $BaI_2$.

The quantity of the catalyst relative to the quantity of benzotrifluoride (abbreviated to BTF) to be chlorinated is variable over a relatively wide range. In general the purpose is accomplished by adjusting the amount of the metal chloride so as to become from 0.0001 to 1.0 mole per mole of BTF subjected to chlorination. A suitable amount of iodine or iodide depends on the amount of the metal chloride and is not strictly limited, but it suffices to use a very small amount of iodine. In general it is suitable that iodine employed as the secondary component of the catalyst, or iodine contained in an iodide employed as the secondary component of the catalyst, amounts to from 0.00001 to 0.1 mole per mole of BTF subjected to chlorination.

It is practically convenient and preferable to perform the process of the invention by first adding the catalyst to BTF kept in a suitable reactor and continuously blowing chlorine gas into the reactor. Though it is possible to dissolve BTF and the catalyst in an organic solvent that does not participate in chlorination reaction, usually it is preferable to use BTF itself and the reaction product as the reaction medium in view of the ease of separation of the chlorinated BTF from the remaining components of the reaction system.

In the process of the invention there is no strict limitation to the reaction temperature. That is, a desired temperature in a wide range from about −20° C. to about 100° C. can be employed. However, it is uneconomical to employ unnecessarily low reaction temperatures because of lowering in the rate of reaction. It is also unfavorable to employ unnecessarily high reaction temperatures because of some increase in the amounts of unwanted by-products other than monochlorobenzotrifluoride and lowering in the selectivity for m-chlorobenzotrifluoride (abbreviated to m-CBTF). Usually it is favorable that the reaction temperature is in the range from about 0° C. to about 40° C. Since the chlorination reaction in this process is an exothermic reaction, there is the need of adequately cooling the reaction system so as to maintain the reaction temperature within a desired range.

In this process, the total quantity of chlorine brought into contact with BTF should not exceed 1 mole per 1 mole of BTF. The use of a larger amount of chlorine will promote excessive chlorination and will result in an increase in the formation of dichlorobenzotrifluoride (abbreviated to DCBTF) isomers and lowering in the selectivity for m-CBTF. The rate of feed of chlorine gas into the reactor has little influence on the yield of m-CBTF and selectivity for m-CBTF.

The invention will further be illustrated by the following nonlimitative examples.

EXAMPLE 1

A cylindrical glass vessel having a capacity of 200 ml was used as reaction vessel. In a bottom section the reaction vessel was formed with an intake opening to which was connected a chlorine gas feed pipe fitted with a glass filter, and the reaction vessel was provided with a thermometer and a reflux condenser.

At room temperature, 1.0 mole (146 g) of BTF was charged into the reaction vessel together with 0.01 moles of iron(III) chloride and 0.005 moles of iodine. Stirring the liquid in the reaction vessel by using a magnetic stirrer, chlorine gas was continuously blown into the vessel for 3.0 hr at a rate of 0.20–0.30 mole/hr to cause BTF to gradually undergo the chlorination reaction. Since the reaction was an exothermic reaction, the reaction vessel was cooled from the outside so as to maintain the reaction temperature in the vessel at 20° C. During the reaction, the reacting liquid was sampled at predetermined time intervals to analyze the composition of the liquid by gas chromatography.

The product of the reaction was a mixture of a major amount of m-CBTF and minor amounts of unreacted BTF, o-CBTF, p-CBTF and dichlorobenzotrifluorides. Table 1A shows the reaction conditions, conversion of BTF, composition of the reaction product, mole ratio of m-CBTF to p-CBTF in the product and average conversion of chlorine gas. The corresponding data obtained in the following Examples 2–8 are also presented in Table 1A.

EXAMPLES 2–8

In these examples $AlCl_3$, $GaCl_3$, $TiCl_4$, $ZrCl_4$, $NbCl_5$, $TaCl_5$ and $WCl_6$ were respectively used as catalyst in place of $FeCl_3$ in Example 1, and the reaction for chlorination of BTF was carried out in the same manner as in Example 1 with the exception that in Examples 2–5 and 8 the reaction time was extended to 4.0 hr.

EXAMPLE 9

The process of Example 1 was modified only in the following items. 0.01 moles of $SbCl_5$ were used in place of $FeCl_3$, and the amount of $I_2$ was decreased to 0.004 moles.

Table 1B shows the reaction conditions and the result obtained in Example 9 together with the corresponding data obtained in Example 1 and the following Examples 10–12.

EXAMPLE 10

The process of Example 9 was modified by decreasing the amount of $SbCl_5$ to 0.007 moles and the amount of $I_2$ to 0.002 moles and raising the reaction temperature to 25° C.

EXAMPLE 11

The process of Example 1 was modified only in that the reaction temperature was maintained within the range from 0° to 5° C.

EXAMPLE 12

The process of Example 1 was modified in that 0.01 moles of KI was used in place of $I_2$ and that the reaction time was extended to 4.0 hr.

TABLE 1A

| | Metal Chloride moles | Iodine Source moles | Reaction Temp. (°C.) | Reaction Time (hr) | Conversion of BTF (mole %) | Composition of Product (mole %) | | | | m-CBTF p-CBTF | Average Conversion of $Cl_2$ (mole %) |
|---|---|---|---|---|---|---|---|---|---|---|---|
| | | | | | | o-CBTF | m-CBTF | p-CBTF | DCBTF | | |
| Ex. 1 | $FeCl_3$ 0.01 | $I_2$ 0.005 | 20 | 3.0 | 72.4 | 2.0 | 57.7 | 3.2 | 9.4 | 18.0 | 99.7 |
| Ex. 2 | $AlCl_3$ 0.01 | $I_2$ 0.005 | 20 | 4.0 | 31.9 | 2.5 | 24.9 | 1.3 | 2.8 | 19.2 | 41.7 |
| Ex. 3 | $GaCl_3$ 0.01 | $I_2$ 0.005 | 20 | 4.0 | 79.9 | 3.4 | 58.5 | 3.0 | 14.0 | 19.5 | 99.9 |
| Ex. 4 | $TiCl_4$ 0.01 | $I_2$ 0.005 | 20 | 4.0 | 45.9 | 4.5 | 35.7 | 2.1 | 2.8 | 17.0 | 59.1 |
| Ex. 5 | $ZrCl_4$ 0.01 | $I_2$ 0.005 | 20 | 4.0 | 70.8 | 4.7 | 54.9 | 2.8 | 8.0 | 19.6 | 70.6 |
| Ex. 6 | $NbCl_5$ 0.01 | $I_2$ 0.005 | 20 | 3.0 | 79.4 | 3.5 | 58.4 | 3.7 | 12.4 | 15.8 | 98.8 |
| Ex. 7 | $TaCl_5$ 0.01 | $I_2$ 0.005 | 20 | 3.0 | 73.7 | 2.8 | 56.7 | 3.5 | 9.8 | 16.2 | 98.3 |
| Ex. 8 | $WCl_6$ 0.01 | $I_2$ 0.005 | 20 | 4.0 | 74.5 | 4.4 | 56.3 | 3.9 | 9.5 | 14.4 | 94.7 |

TABLE 1B

| | Metal Chloride moles | Iodine Source moles | Reaction Temp. (°C.) | Reaction Time (hr) | Conversion of BTF (mole %) | Composition of Product (mole %) | | | | m-CBTF / p-CBTF | Average Conversion of Cl₂ (mole %) |
|---|---|---|---|---|---|---|---|---|---|---|---|
| | | | | | | o-CBTF | m-CBTF | p-CBTF | DCBTF | | |
| Ex. 1 | FeCl₃ 0.01 | I₂ 0.005 | 20 | 3.0 | 72.4 | 2.0 | 57.7 | 3.2 | 9.4 | 18.0 | 99.7 |
| Ex. 9 | SbCl₅ 0.01 | I₂ 0.004 | 20 | 3.0 | 77.5 | 2.4 | 57.9 | 3.6 | 13.2 | 16.1 | 99.8 |
| Ex. 10 | SbCl₅ 0.007 | I₂ 0.002 | 25 | 3.0 | 76.3 | 2.3 | 58.1 | 3.7 | 12.9 | 15.7 | 99.8 |
| Ex. 11 | FeCl₃ 0.01 | I₂ 0.005 | 0-5 | 3.0 | 63.5 | 1.7 | 53.0 | 2.4 | 6.2 | 22.1 | 99.5 |
| Ex. 12 | FeCl₃ 0.01 | KI 0.01 | 20 | 4.0 | 71.2 | 2.7 | 56.8 | 3.9 | 7.6 | 14.6 | 79.7 |
| Ref. 1 | FeCl₃ 0.01 | — | 20 | 5.0 | 70.2 | 5.3 | 55.6 | 4.9 | 4.2 | 11.3 | 60.1 |
| Ref. 2 | — | I₂ 0.01 | 20 | 1.0 | 1.3 | 0.4 | 0.5 | 0.3 | | 1.7 | 5.5 |

REFERENCE 1

In the reaction vessel mentioned in Example 1, 1.0 mole of BTF was subjected to reaction with chlorine gas in the presence of 0.01 moles of FeCl₃ generally in the same manner as in Example 1 but without using iodine or any iodine compound. The reaction conditions and the result are presented in Table 1B together with the data obtained in the following Reference 2.

REFERENCE 2

The process of Example 1 was generally repeated but without using FeCl₃ or any alternative metal chloride, though 0.01 moles of iodine was used.

What is claimed is:

1. A process of preparing m-chlorobenzotrifluoride by reacting benzotrifluoride and chlorine in the presence of a catalyst with a selectivity sufficient to produce a ratio of m-chlorobenzotrifluoride to p-chlorobenzotrifluoride product of at least about 14, wherein said catalyst comprises a combination of at least one metal chloride selected from the group consisting of iron trichloride, gallium trichloride, antimony pentachloride, niobium pentachloride and tantalum pentachloride, and iodine, said at least one metal chloride and said iodine being present in amounts of at least 0.007 mole and at least 0.002 mole, respectively, per mole of benzotrifluoride, and wherein the reaction is maintained at a temperature of from about 0° to about 40° C., and the mole ratio of chlorine to benzotrifluoride does not exceed about 1.0.

2. A process according to claim 9, wherein said reaction is carried out by continuously introducing chlorine gas into a reactor in which benzotrifluoride and said catalyst are maintained.

3. A process of preparing m-chlorobenzotrifluoride comprising reacting benzotrifluoride and chlorine in the presence of a meta-selective catalyst comprising a combination of at least one metal chloride selected from the group consisting of iron trichloride, gallium trichloride, antimony pentachloride, niobium pentachloride and tantalum pentachloride, and iodine, said catalyst being present in an amount effective to produce a ratio of m-benzotrifluoride to p-benzotrifluoride product of at least about 14, and wherein the reaction is maintained at a temperature of from about 0° to about 40° C., and the mole ratio of chlorine to benzotrifluoride does not exceed about 1.0.

* * * * *